US012558545B2

(12) United States Patent
Humayun et al.

(10) Patent No.: US 12,558,545 B2
(45) Date of Patent: Feb. 24, 2026

(54) SYSTEM AND METHOD FOR RESTORING COLOR PERCEPTION TO THE BLIND

(71) Applicant: UNIVERSITY OF SOUTHERN CALIFORNIA, Los Angeles, CA (US)

(72) Inventors: Mark S. Humayun, Los Angeles, CA (US); Lan Yue, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 371 days.

(21) Appl. No.: 18/026,443

(22) PCT Filed: Sep. 24, 2021

(86) PCT No.: PCT/US2021/052071
§ 371 (c)(1),
(2) Date: Mar. 15, 2023

(87) PCT Pub. No.: WO2022/067112
PCT Pub. Date: Mar. 31, 2022

(65) Prior Publication Data
US 2023/0355973 A1    Nov. 9, 2023

Related U.S. Application Data

(60) Provisional application No. 63/082,699, filed on Sep. 24, 2020.

(51) Int. Cl.
*A61N 1/36*        (2006.01)
*A61F 9/08*        (2006.01)
(Continued)

(52) U.S. Cl.
CPC ............ *A61N 1/36046* (2013.01); *A61F 9/08* (2013.01); *A61N 1/0543* (2013.01); *A61N 1/36196* (2013.01); *A61N 1/37217* (2013.01)

(58) Field of Classification Search
CPC ............ A61N 1/36046; A61N 1/36196; A61N 1/0543; A61F 9/08
See application file for complete search history.

(56) References Cited

U.S. PATENT DOCUMENTS 5,895,415 A * 4/1999 Chow ...................... A61N 1/05
                                                            607/148
5,944,747 A * 8/1999 Greenberg ......... A61N 1/36046
                                                            607/54

(Continued)

FOREIGN PATENT DOCUMENTS

JP        2001-285679        10/2001
KR    10-2009-0103534        10/2009
WO    WO 2012-017426          2/2012

OTHER PUBLICATIONS

International Search Report and Written Opinion (mailing date Jan. 14, 2022) for International PCT Patent Application No. PCT/US2021/052071, filed Sep. 24, 2021.

(Continued)

*Primary Examiner* — Eric D. Bertram

(57)        ABSTRACT

A system and method are disclosed for causing or enhancing the perception of color in a blind or visually impaired person. The system may comprise: an electromagnetic stimulation device associated with the blind or visually impaired person; and a visualization device for receiving an image and detecting a color of an object in the image, wherein the electromagnetic stimulation device is configured to stimulate the blind or visually impaired person based on a parameter of electromagnetic stimulation that varies based on the color detected by the visualization device. The method may comprise: varying a parameter of electromagnetic stimulation of an electromagnetic stimulation device, associated with an eye of the blind or visually impaired person, based on which color is detected by a visualization (Continued)

device that is used in conjunction with the electromagnetic stimulation device; and stimulating the eye with the electromagnetic stimulation device according to the parameter of electromagnetic stimulation.

11 Claims, 5 Drawing Sheets

(51) Int. Cl.
*A61N 1/05* (2006.01)
*A61N 1/372* (2006.01)

(56) References Cited

U.S. PATENT DOCUMENTS

| | | | | |
|---|---|---|---|---|
| 6,230,057 B1 * | 5/2001 | Chow | ..................... | A61N 1/05 |
| | | | | 607/148 |
| 7,257,446 B2 * | 8/2007 | Greenberg | ........... | A61N 1/0543 |
| | | | | 607/54 |
| 7,668,599 B2 * | 2/2010 | Greenberg | ........... | A61N 1/0543 |
| | | | | 607/54 |
| 8,706,243 B2 * | 4/2014 | Gefen | .................. | A61N 1/3787 |
| | | | | 607/53 |
| 9,205,257 B1 * | 12/2015 | Coley | ..................... | A61F 2/141 |
| 9,265,945 B2 * | 2/2016 | Gross | .................. | H10F 39/8063 |
| 10,984,234 B2 * | 4/2021 | Peng | ....................... | A61F 2/141 |
| 2002/0038134 A1 * | 3/2002 | Greenberg | ......... | A61N 1/36046 |
| | | | | 607/1 |
| 2002/0091421 A1 * | 7/2002 | Greenberg | ......... | A61N 1/36046 |
| | | | | 607/54 |
| 2003/0181957 A1 | 9/2003 | Greenberg et al. | | |
| 2007/0016425 A1 | 1/2007 | Ward | | |
| 2009/0076421 A1 | 3/2009 | Grant, Jr. | | |
| 2019/0070064 A1 * | 3/2019 | Hogle | ................... | G06V 10/44 |

OTHER PUBLICATIONS

International Preliminary Report on Patentability dated Mar. 28, 2023, in corresponding International Application No. PCT/US2021/052071 filed Sep. 24, 2021; 5 pages.

The Supplementary European search report and the European search opinion dated Sep. 17, 2024, in corresponding European Application No. EU21873561.1; 5 pages.

\* cited by examiner

SYSTEM AND METHOD FOR RESTORING COLOR PERCEPTION TO THE BLIND

PRIORITY CLAIM

This application claims priority to U.S. provisional patent application No. 63/082,699, titled "System and Method for Restoring Color Perception to the Blind", filed Sep. 24, 2020. The '699 disclosure is incorporated here by reference in its entirety for all purposes.

FIELD

This disclosure generally relates to system and method for causing or enhancing the perception of color in a blind or visually impaired person, and more particularly, to varying electromagnetic stimulation in an electromagnetic stimulation device to cause or enhance the perception of color.

BACKGROUND

Various efforts have been made to help people who have lost their vision (complete loss of vision, or significant loss of vision) to regain some of their ability to perceive the surrounding world. In particular, bioelectronic retinal prostheses that stimulate the remaining inner retinal neurons, bypassing severely damaged photoreceptors, have been demonstrated to restore some aspect of vision in blind or visually impaired people. However, systems used to date are pixilated, grainy, and monochromatic, leaving the blind or visually impaired person with a significant lack of information about their surroundings. Thus, a strong need exists for a system that can provide more information to a blind person to enhance their ability to perceive their surroundings.

SUMMARY

A method of causing or enhancing the perception of color in a blind or visually impaired person is disclosed. The method may comprise: varying a parameter of electromagnetic stimulation of an electromagnetic stimulation device, associated with an eye of the blind or visually impaired person, based on which color is detected by a visualization device that is used in conjunction with the electromagnetic stimulation device; and stimulating the eye with the electromagnetic stimulation device according to the parameter of electromagnetic stimulation.

A system for causing or enhancing the perception of color in a blind or visually impaired person is disclosed. The system may comprise: an electromagnetic stimulation device associated with the blind or visually impaired person; and a visualization device for receiving an image and detecting a color of an object in the image, wherein the electromagnetic stimulation device is configured to stimulate the blind or visually impaired person based on a parameter of electromagnetic stimulation that varies based on the color detected by the visualization device.

In an example embodiment, an article of manufacture is disclosed. The article of manufacture may include a non-transitory, tangible computer readable storage medium having instructions stored thereon that, in response to execution by a processor, cause the processor to cause or enhance the perception of color in a blind or visually impaired person, the operations comprising: varying a parameter of electromagnetic stimulation of an electromagnetic stimulation device, associated with an eye of the blind or visually impaired person, based on which color is detected by a visualization device that is used in conjunction with the electromagnetic stimulation device; and stimulating the eye with the electromagnetic stimulation device according to the parameter of electromagnetic stimulation.

BRIEF DESCRIPTION OF DRAWINGS

A more complete understanding of the present disclosure may be derived by referring to the detailed description and claims when considered in connection with the Figures, wherein like reference numbers refer to similar elements throughout the Figures, and:

DETAILED DESCRIPTION

Figure 1:
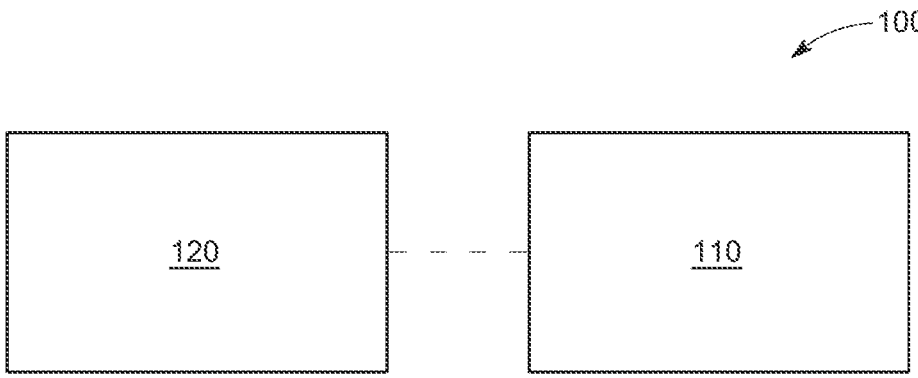
FIG. 1 is an exemplary high-level overview of a system for causing or enhancing the perception of color in a blind person, in accordance with various embodiments.

In accordance with various example embodiments, a method for causing or enhancing the perception of color in a blind or visually impaired person is described herein. The method comprises varying a parameter of electromagnetic stimulation of an electromagnetic stimulation device, associated with the blind or visually impaired person, based on which color is detected by a visualization device that is used in conjunction with the electromagnetic stimulation device; and stimulating the eye with the electromagnetic stimulation device according to the parameter of electromagnetic stimulation. In an example embodiment, the method and system disclosed herein facilitate frequency modulated bioelectronic color perception.

In an example embodiment, the patient is a person that is blind. In another example embodiment, the patient is a person that is visually impaired. In example embodiments, the person may be blind due to retinitis pigmentosa (RP) or Usher Syndrome-2 (USH2). Moreover, the person may be blind due to other disease, defect, or injury. In accordance with various embodiments, the blind person has no light perception or bare light perception before applying visual enhancement tools. For the sake of brevity, when used herein, references to a blind person shall be understood to include a 'visually impaired person.' Moreover, the system and method described herein may be useful to any person in which causing or enhancing the perception of color would be useful, to the extent the solution is a net positive for the patient's visual perception situation. The system and method enable enhanced color perception, which enables a blind person to discriminate different colors in different areas of the visual field, facilitates integrating color information with spatial information, facilitates quicker and more accurate object recognition, target localization and visually guided orientation, supplements for the loss of spatial information, facilitates edge detection of colored objects, assists in distinguishing two objects of similar shape, and facilitates quicker visual field scanning and more accurate visual field segmentation.

As noted above, in patients blinded by retinitis pigmentosa (RP), bioelectronic retinal prostheses that stimulate the remaining inner retinal neurons, bypassing severely damaged photoreceptors, have been demonstrated to restore some vision. These implants encode luminance of the visual scene into the electrical stimulation. However, these systems do not provide any chromatic information (no color information). Yet color plays a very important role in visual processing when it comes to recognizing objects and orienting to the environment. This is especially important at low spatial resolution generated by the present day retinal prostheses. For example, present day bioelectronic retinal prostheses can provide grainy/pixelated images of an apple and an orange, but it may be difficult to distinguish these two objects from each other and/or to identify these objects without color or without significantly higher resolution in the image detection.

In an example embodiment, the systems and methods described herein are configured to enhance perception of color in a blind or visually impaired person. Alternatively, the systems and methods described herein may be configured to restore perception of color in a blind or visually impaired person. The system may be configured to increase the visual content information perceived by a blind or visually impaired person, to aid in orientation and mobility as well as object detection by providing color content information about the objects in the visual field captured by a visualization device. Stated another way, the systems and methods described herein are configured to increase informational content without increasing the number of pixels/spatial resolution. This may be achieved by varying a parameter of electromagnetic stimulation. In an example embodiment, the method is implemented in a retinal prostheses (or visual prostheses) to provide limited color sensation as an extra dimension of vision. In accordance with various attributes described herein, the system and method may facilitate "color vision," and/or "retinal stimulation."

With reference now to FIG. 1, a system 100 is disclosed for causing or enhancing the perception of color in a blind or visually impaired person. In an example embodiment, the system 100 comprises an electromagnetic stimulation device 110 and a visualization device 120.

Visualization Device 120

In an example embodiment, the visualization device 120 is configured to receive an image and detect a color in at least a portion of that image. In an example embodiment, the visualization device 120 comprises a camera. The visualization device 120 may, for example comprise a digital camera or video camera, capable of viewing a field of view and capturing one or more images representative of the field of view and objects therein. In other example embodiments, the visualization device 120 may comprise glasses configured to be worn on the head like typical glasses, with a camera mounted to the glasses for receiving images. In other example embodiments, the visualization device 120 may be worn on a hat or helmet, such as implemented with a video system for recording outdoor adventures. Moreover, the visualization device 120 may comprise any suitable video/camera system for receiving images of the area surrounding a blind person. The visualization device 120 may be configured to receive images from the vantage point of the blind person.

In an example embodiment, the visualization device 120 further includes a processor. In an example embodiment, the processor is configured to receive the image(s) and to identify color in the image(s). In an example embodiment, the visualization device 120 is configured to cause the electromagnetic stimulation device 110 to vary a parameter of electromagnetic stimulation based on the color in the image received by the visualization device 120.

In an example embodiment, the visualization device 120 may be configured to send a signal to the electromagnetic stimulation device 110 that causes the visualization device 120 to vary a parameter of electromagnetic stimulation based on the color in the image received by the visualization device 120. In an example embodiment, as described further below, the visualization device 120 wirelessly instructs the electromagnetic stimulation device 110 (e.g., the implant) to change the stimulation of the electrical pulses delivered to the retina through the electrodes that correspond to the camera image. Stated another way, the system can be configured to stimulate individual electrodes, in the electromagnetic stimulation device, at specified frequencies of stimulation to cause perception of color at a location of the retina associated with certain electrodes, and no color or a different color at other electrodes, corresponding to the visualization device image.

In an example embodiment, the visualization device 120 comprises a memory or a database for associating a particular color with a parameter of electromagnetic stimulation. Thus, in an example embodiment, the visualization device 120 may be configured to receive the image, identify a color of an object in the image, look up the parameter of electromagnetic stimulation in the memory based on the color of the object in the image, and send the parameter of electromagnetic stimulation to the electromagnetic stimulation device 110.

Electromagnetic Stimulation Device 110

In an example embodiment, the electromagnetic stimulation device 110 may be configured to vary a parameter of electromagnetic stimulation based on the signal from the visualization device 120.

In an example embodiment, the parameter of electromagnetic stimulation is a frequency of stimulation. In this example embodiment, varying the parameter of electromagnetic stimulation of the electromagnetic stimulation device 110 comprises frequency modulation of stimulation of the electromagnetic stimulation device 110. In one example embodiment, the frequency of electromagnetic stimulation is in the range of 15 Hz to 25 Hz for the color yellow, and the frequency of electromagnetic stimulation is in the range of 60 to 120 Hz for the color blue. The color gold may similarly be perceived by electromagnetic stimulation in the range of 15 Hz to 25 Hz, and the color purple may similarly be perceived by electromagnetic stimulation in the range of 60 to 120 Hz. Moreover, each visible color may be associated with a range of frequency of electrical stimulation. Thus, in an example embodiment, the electromagnetic stimulation device 110 is configured to stimulate the blind person by modulating the frequency of electromagnetic stimulation to a frequency associated with the color detected by the visualization device 120. Stated another way, in an example embodiment, the system and method are configured to generate color perception in a photoreceptor-less retina.

In one example embodiment, the frequency of stimulation for a specific color is set at a specific frequency, a frequency that is used for every individual who uses the electromagnetic stimulation device 110. In this example embodiment, this frequency is suitable for helping most users to perceive that color.

In other example embodiments, the frequency of stimulation for a specific color is set at a frequency that works best for the particular individual using the system to enhance color perception. As described further below, the user may test the system on known colors to identify a frequency that best causes perception of each known color and then once a desired frequency has been identified for the individual, that frequency is saved to be used with that corresponding color. Thus, in an example embodiment, the electromagnetic stimulation device 110 is configured for personalized tuning of the parameter of electromagnetic stimulation, such that the frequency of stimulation provides optimal perception of a color detected by the visualization device 120 for each individual blind or visually impaired person.

In accordance with aspects of the present disclosure, the electromagnetic stimulation device 110 is associated with the blind person. This association can be made in a number of ways. For example, in an example embodiment, the electromagnetic stimulation device 110 is an implant attached to a retina. In another example embodiment, the electromagnetic stimulation device 110 is an implant placed in and around the eye (i.e., subretinal, suprachoroidal, extraocular on the sclera). In another example embodiment, the electromagnetic stimulation device 110 comprises electrodes attached to a retina of the eye of the blind person.

Thus, in accordance with an example embodiment, the parameter of electromagnetic stimulation is a frequency of stimulation of the retinal implant device, and varying the parameter of electromagnetic stimulation of the electromagnetic stimulation device 110 comprises frequency modulation of stimulation of the retinal implant device.

However, in other example embodiments, the electromagnetic stimulation device 110 comprises electrodes attached to any part of the visual system. In a first example embodiment, the 'visual system' comprises an optic nerve. In a second example embodiment, the 'visual system' comprises a lateral geniculate nucleus of the blind person. In a third example embodiment, the 'visual system' comprises a visual cortex of the brain of the blind person. Moreover, the electromagnetic stimulation device 110 may be attached to any part of the blind person associated with vision. Thus, in an example embodiment, the electromagnetic stimulation device 110 is attached to and stimulates the visual system with frequency modulation based on color in the images detected by the visualization device 120, in accordance with the disclosure herein.

Moreover, in other example embodiments, the electromagnetic stimulation device 110 comprises electrodes attached to any sensory part of the human body of the blind person. For example, the sensory part of the human body may comprise at least one of: the skin, the hearing pathway (ear, acoustic nerve), the smell pathway (nose), and the taste pathway (mouth, tongue). Moreover, the sensory part may be any part of the human body with a significant and dense network of sensory nerves. In these example embodiments, these and similar sensory pathways in a human body can provide sensory substitution for lost vision. Thus, in an example embodiment the electromagnetic stimulation device 110 is attached to and stimulates one or more of these sensory parts with frequency modulation based on color in the images detected by the visualization device 120, in accordance with the disclosure herein.

In an example embodiment, the visualization device 120 is configured to cause the retinal implant to vary a parameter of electromagnetic stimulation based on the color in the image received by the visualization device 120. This can be done by the visualization device 120 determining how to vary the parameter based on the color in the image and commanding the electromagnetic stimulation device 110 to vary the parameter accordingly. However, in other example embodiments, various functions described herein as performed by the visualization device 120 can be performed by the electromagnetic stimulation device 110. Moreover, various functions described herein as performed by either the visualization device 120 or the electromagnetic stimulation device 110 can be performed in a distributed manner, such as via cloud servers, remote computers, portable electronic devices, and the like.

By way of example, the system 100 may be similar to the Argus II product by Second Sight Medical Products, comprising an epiretinal implant that converts visual scenes into electrical stimuli that are delivered via an array of 6×10 electrodes to the retina. The array of electrodes is attached to the inner surface of the retina. For example, the array of electrodes may be attached near the ganglion cell layer, implanted in the macula straddling the fovea, with most electrodes in similar parafoveal locations superior temporal to the optic disc. In this example embodiment, the electrodes of the array are 225 micro meters in diameter, and the device is used in a way to modulate the frequency of stimulation. In this example, the pulse width of 0.45 ms is used with a charge density limit of 442 micro C/cm^2 per phase. In another example embodiment, the Intelligent Medical Implant by Pixium Vision can be used with modulation of the frequency of stimulation. Moreover, any suitable implant/vision system can be used with any suitable pulse width and other settings, with modulation of the frequency of stimulation. In one example embodiment, the pulses are biphasic pulses. The biphasic pulses may be used to stimulate neural tissue like the retina, using both cathodic and anodic phases of the pulse.

In accordance with an example embodiment, the visualization device 120 is configured to send a wireless command to the implanted electronics to stimulate at the appropriate frequency. Thus, in accordance with various example embodiments, the wireless command can be driven by software or hardware.

Wireless

In accordance with various example embodiments, the electromagnetic stimulation device 110 and the visualization device 120 further comprise wireless communication devices for communication between the electromagnetic stimulation device 110 and the visualization device 120. In an example embodiment, the visualization device 120 is configured to control the variation of the parameter of electromagnetic stimulation via a wireless signal to the electromagnetic stimulation device 110. In one example embodiment, the visualization device 120 sends a wireless signal to the electromagnetic stimulation device 110 that sets the parameter. In another example embodiment, the wireless signal conveys to the electromagnetic stimulation device 110 the color of the object.

In an example embodiment, the wireless communication devices are one of: a radio frequency signal, a Bluetooth signal, a Wi-Fi signal, and an optical signal. However, any suitable wireless signal can be used to communicate between the electromagnetic stimulation device 110 and the visualization device 120. In an example embodiment, the wireless communication devices may comprise a transceiver, transmitter and/or receiver. In the optical method, the implant receiver would further comprise a photodiode or the like, optically sensitive to commands from the visualization device 120.

Figure 3:
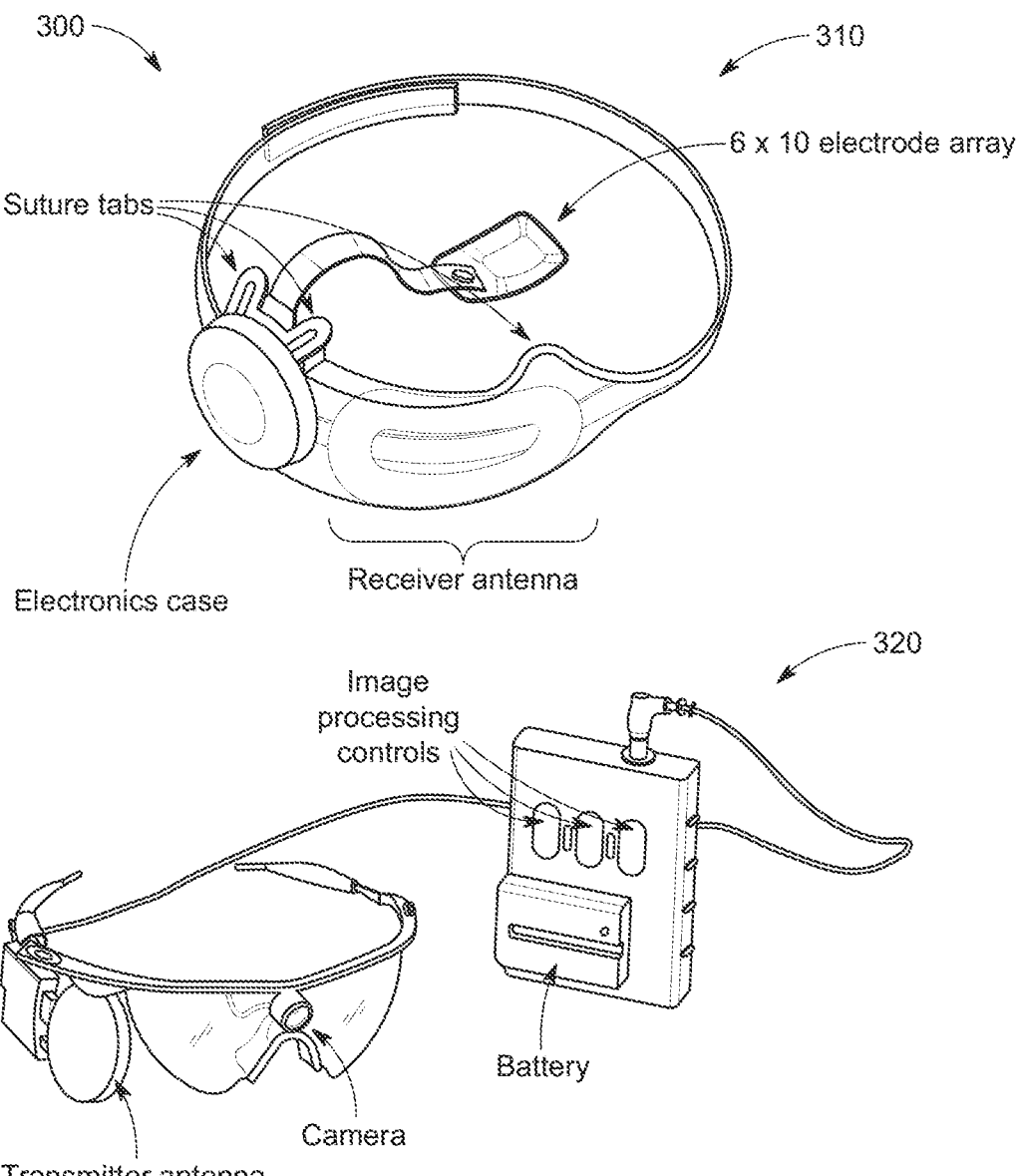
FIG. 3 is an illustration of an example system of FIG. 1.

With reference now to FIG. 3, a system 300 is illustrated for causing or enhancing the perception of color in a blind or visually impaired person. In an example embodiment, the system 300 comprises an electromagnetic stimulation device 310 and a visualization device 320. In an example embodiment, the electromagnetic stimulation device 310 may comprise an electrode array (such as, for example, the 6×10 electrode array illustrated). In an example embodiment, the electromagnetic stimulation device 310 may comprise suture tabs for securing the device in place. In an example embodiment, the electromagnetic stimulation device 310 may comprise a receiver antenna for receiving communication signals from the visualization device 320. In an example embodiment, the electromagnetic stimulation device 310 may comprise an electronics case for enclosing a processor and/or electronics for causing the stimulation of electrodes in the electrode array. Moreover in an example embodiment, the visualization device 320 may comprise a camera. The visualization device 320 may further comprise a transmitter antenna, image processing controls, a battery and/or the like. The system 300 may be configured to operate as disclosed herein to vary a frequency of stimulation based on color(s) in images received by the camera.

Method

Figure 2A:
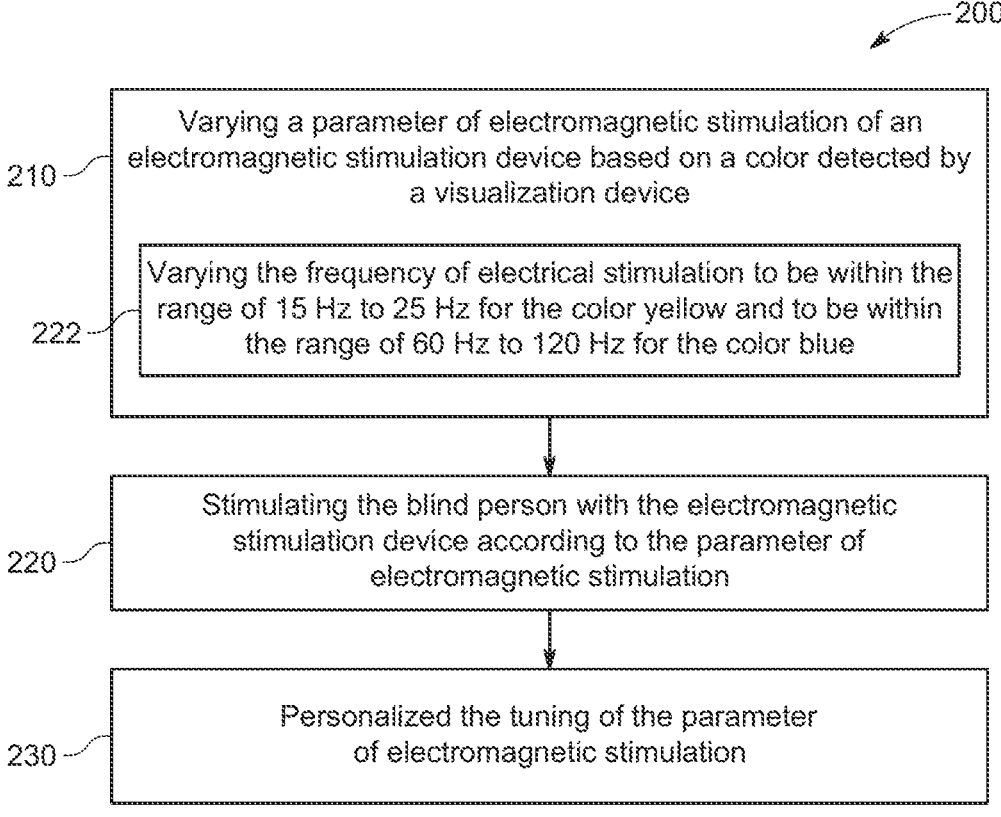
FIGS. 2A, 2B, and 2C are flow diagrams illustrating an exemplary method(s) for causing or enhancing the perception of color in a blind person, in accordance with various embodiments.

With reference now to FIG. 2A, a method 200 may be configured to cause or enhance the perception of color in a blind or visually impaired person. In an example embodiment, method 200 may comprise the step 210 of varying a parameter of electromagnetic stimulation of an electromagnetic stimulation device 110, associated the blind or visually impaired person, based on which color is detected by a visualization device 120 that is used in conjunction with the electromagnetic stimulation device 110. The method may further comprise the step 220 of stimulating the blind person with the electromagnetic stimulation device 110 according to the parameter of electromagnetic stimulation. In an example embodiment, the parameter of electromagnetic stimulation is a frequency of stimulation. In this example embodiment, varying the parameter of electromagnetic stimulation of the electromagnetic stimulation device 110 comprises frequency modulation of stimulation of the electromagnetic stimulation device 110.

In an example embodiment, the frequency of electrical stimulation is in the range of 15 Hz to 25 Hz for the color yellow, and wherein the frequency of electrical stimulation is in the range of 60 to 120 Hz for the color blue. Thus the method may comprise the sub step 222 of varying the frequency of electrical stimulation to be within the range of 15 Hz to 25 Hz for the color yellow and to be within the range of 60 Hz to 120 Hz for the color blue.

In an example embodiment, varying a parameter of electromagnetic stimulation may be caused by the visualization device 120 or the electromagnetic stimulation device 110. In an example embodiment, varying the parameter of electromagnetic stimulation further comprises controlling the variation of the parameter of electromagnetic stimulation via a wireless signal to the electromagnetic stimulation device 110. In an example embodiment, the wireless signal is provided in response to what is detected by the visualization device 120. In another example embodiment, the wireless signal is one of: a radio frequency signal, a Bluetooth signal, a Wi-Fi signal, and an optical signal.

In accordance with an example embodiment, the electromagnetic stimulation device 110 comprises electrodes attached to a retina of an eye. Thus, the method may further comprise the step of attaching a retinal implant to the back of the retina.

In accordance with another example embodiment, the electromagnetic stimulation device 110 comprises electrodes attached to any part of the blind person's visual system. For example, the blind person's visual system may comprise at least one of: an optic nerve, a lateral geniculate nucleus, and a visual cortex of the brain. Thus, the method may further comprise the step of attaching electrodes to any part of the blind person's visual system.

In yet another example embodiment, the electromagnetic stimulation device 110 comprises electrodes attached to any sensory part of the human body of the blind person. For example, the sensory part of the human body may comprise at least one of: the skin, the hearing pathway (ear, acoustic nerve), the smell pathway (nose), and the taste pathway (mouth, tongue). Thus, the method may further comprise the step of attaching electrodes to any sensory part of the blind person's body.

Personalized Tuning

In accordance with an example embodiment, the method further comprises personalized tuning of the parameter of electromagnetic stimulation step 230, such that the frequency of stimulation provides optimal perception of a color detected by the visualization device 120 for each individual blind or visually impaired person.

Figure 2B:
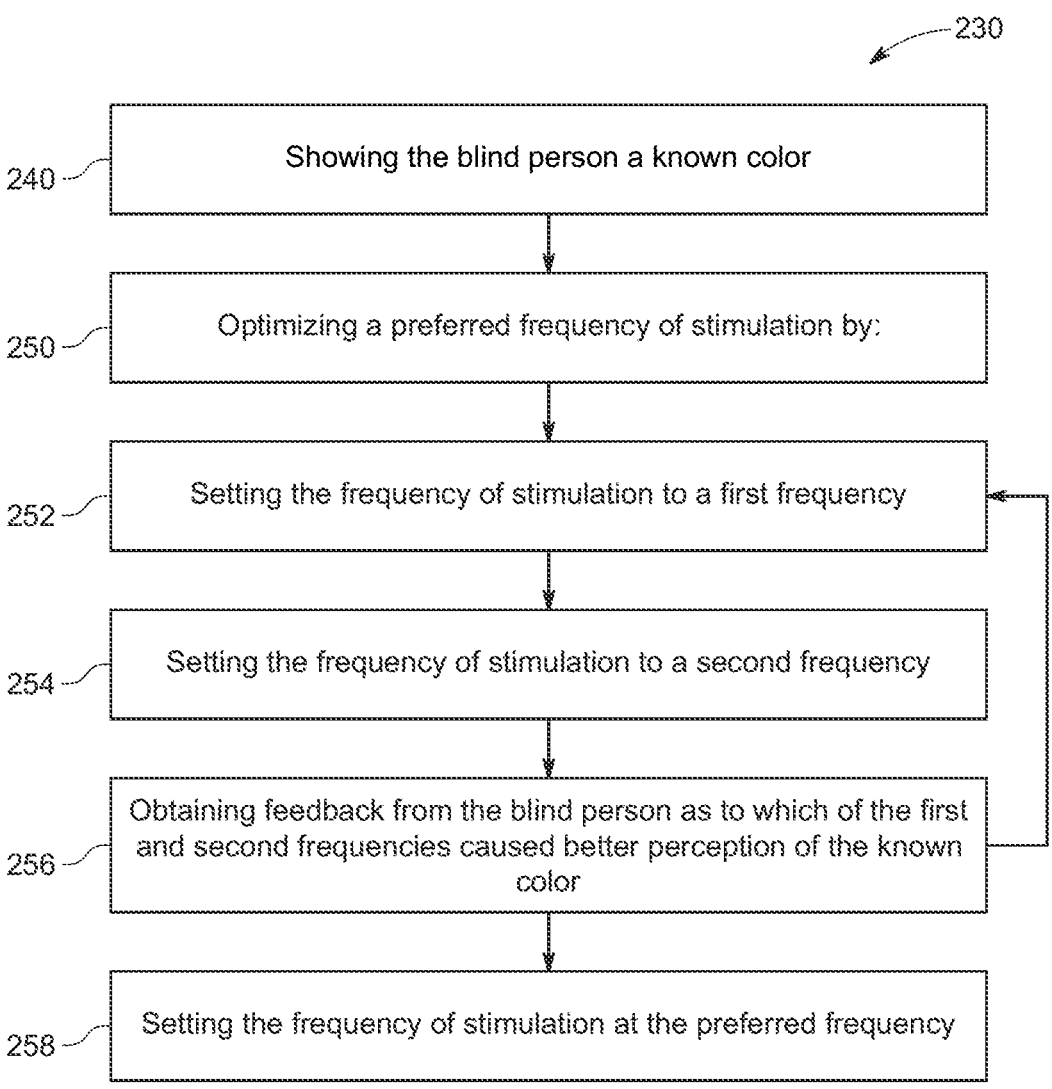

In this example embodiment, referring now to FIG. 2B, personalized tuning (step 230) may further comprise: showing the blind or visually impaired person a known color (step 240); optimizing a preferred frequency of stimulation (step 250) by repeating the process of: setting the frequency of stimulation to a first frequency (step 252); setting the frequency of stimulation to a second frequency (step 254); obtaining feedback from the blind person as to which of the first frequency and the second frequency caused better perception of the known color, and using the response to set the preferred frequency (step 256); and setting the frequency of stimulation at the preferred frequency (step 258). It is noted that any suitable method of optimizing the frequency associated with a color may be used.

Figure 2C:
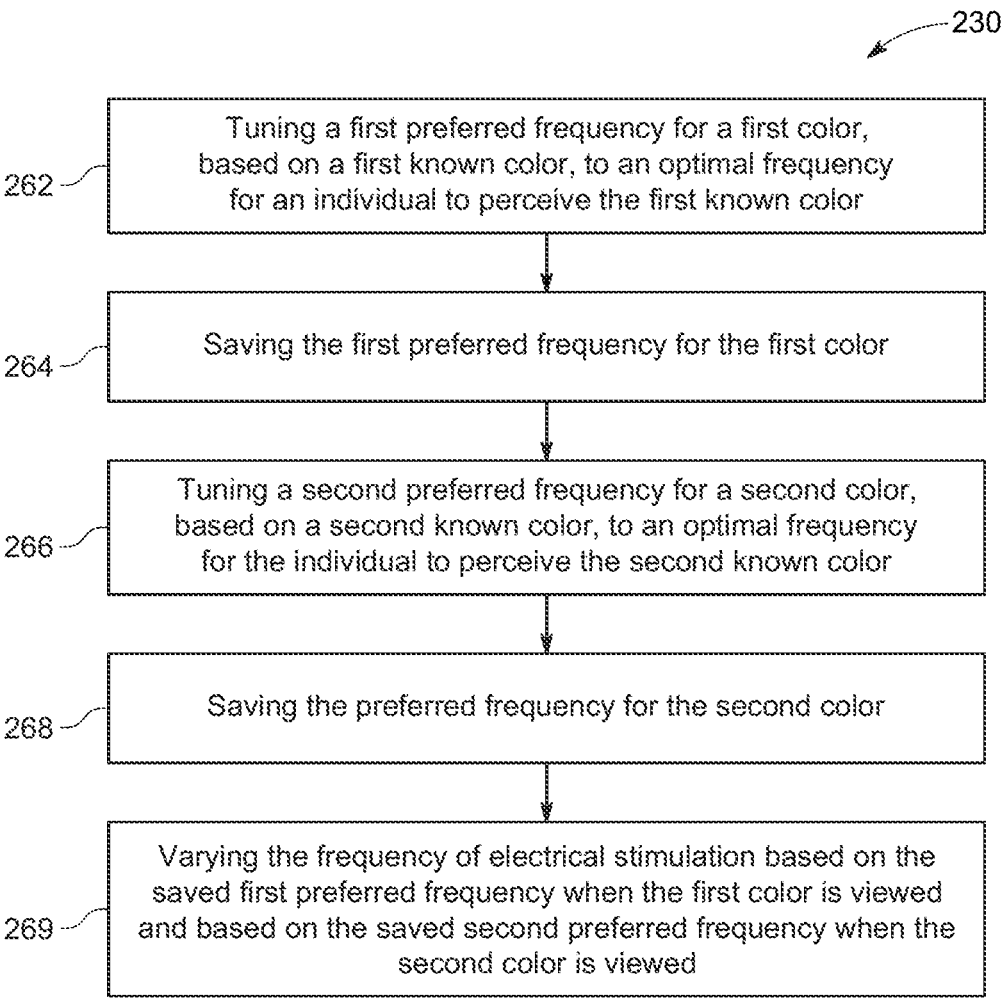

In accordance with another example embodiment, referring now to FIG. 2C, personalized tuning step 230 may further comprise: tuning a first preferred frequency for a first color, based on a first known color, to an optimal frequency for an individual to perceive the first known color (step 262); saving the first preferred frequency for the first color (step 264); tuning a second preferred frequency for a second color, based on a second known color, to an optimal frequency for the individual to perceive the second known color (step 266); saving the preferred frequency for the second color (step 268); varying the frequency of electrical stimulation of the electromagnetic stimulation device 110 based on the saved first preferred frequency when the first color is viewed by the visualization device, and based on the saved second preferred frequency when the second color is viewed by the visualization device (step 269).

In an example embodiment, the frequency modulation is based on a first frequency associated with a first color and a second frequency associated with a second color. Moreover, any suitable number of different frequencies can each be associated with a unique color. Thus, the frequency of stimulation is modulated from the first frequency to the second frequency in accordance with the color perceived by the vision device. Or the frequency of stimulation is modulated to correspond to the color perceived by the vision device. Moreover, when the first color appears in part of the image and the second color appears in a different part of the image, a first electrode or first set of electrodes are stimulated at the first frequency and a second electrode or second set of electrodes are stimulated at the second frequency. In each case, the stimulation waveform will have an amplitude, frequency and pulse width. In an example embodiment, the pulse width may be from 0.2 ms to 2 ms, from 0.2 ms to 1.5 ms, or 0.4 ms to 0.5 ms. However, any suitable pulse width may be used.

It is noted that when tuning an implant to a specific patient, in some example embodiments, the electromagnetic stimulation device 110 can have each electrode tuned to that patient and the specific portion of the sensory system (e.g. specific portion of the retina) to which that electrode is attached. In this manner, the electromagnetic stimulation device 110 is configured to adapt to the differences between the different locations in the retina, where each retina location may respond better to a slightly different frequency.

In an example embodiment, spatially matched multi-color perception is generated by simultaneous stimulation of paired electrodes, with the frequency of stimulation of one electrode differing from the frequency of stimulation of the other electrode. Stated another way, the system 100 is configured to encode color information extracted from the image into frequency modulated electrical stimulation.

One or more of the components of the system 100 may include software, hardware, a platform, app, micro-app, algorithms, modules, etc. The app may operate on any platform such as, for example, the IOS or Android platforms.

In accordance with various example embodiments, the tuning of the parameter and/or the identification of colors in the images may be trained by the use of artificial intelligence, machine learning and other algorithms. Training may involve the use of data from a large patient population, and this data can be processed to adjust the frequencies used for various colors over time and in accordance with patient assessments. The frequency settings may be adjusted (for individuals or for overall populations) over time, to account for changes in the individuals or further data. Thus, a subject may initially have a first frequency for a first color, but an update may assign a second frequency for the first color at a later point in time.

The system 100 may utilize artificial intelligence.

In various embodiments, components, modules, and/or engines of system 100 may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any or any combination of programming or scripting languages such as C, C++, C #, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

The system and method are described herein with reference to screen shots, block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like.

In various embodiments, the software elements of the system may also be implemented using a JAVASCRIPT® run-time environment configured to execute JAVASCRIPT® code outside of a web browser. For example, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEBSPHERE® MQ™ (formerly MQSeries) by IBM®, Inc. (Armonk, NY) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, shopping, making to-do lists, setting alarms, streaming podcasts, playing audiobooks, and providing real time information, such as news. The ALEXA®, GOOGLE HOME®, and HOMEPOD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the embodiments are directed toward one or more computer systems capable of carrying out the functionalities described herein. The computer system includes one or more processors. The processor is connected to a communication infrastructure (e.g., a communications bus, cross-over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a removable memory chip (such as an erasable programmable read only memory (EPROM), programmable read only memory (PROM)) and associated socket, or other removable storage units and interfaces, which allow software and data to be transferred from the removable storage unit to a computer system.

The computer system or visualization device 120 may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

In various embodiments, the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, NY), various database products available from ORACLE® Corporation (Redwood Shores, CA), MICROSOFT ACCESS® or MICROSOFT SQL SERVER® by MICROSOFT® Corporation (Redmond, Washington), MYSQL® by MySQL AB (Uppsala, Sweden), MONGODB®, Redis, Apache Cassandra®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825;

other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions, such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data, but instead the appropriate action may be taken by providing to the user, at the stand-alone device, the appropriate option for the action to be taken. The system may contemplate a data storage arrange-ment wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.ha-doop.apache.org/docs.

As used herein, the term "network" includes any cloud, cloud computing system, or electronic communications sys-tem or method which incorporates hardware and/or software components. Communication among the parties may be accomplished through any suitable communication chan-nels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area net-work (WAN), virtual private network (VPN), networked or linked devices, keyboard, mouse, and/or any suitable com-munication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

Any communication, transmission, and/or channel dis-cussed herein may include any system or method for deliv-ering content (e.g. data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.), a uniform resource locator ("URL"), a document (e.g., a MICROSOFT® Word or EXCEL™, an ADOBE® Portable Document Format (PDF) document, etc.), an "ebook," an "emagazine," an application or microapplication (as described herein), an short message service (SMS) or other type of text message, an email, a FACEBOOK® message, a TWITTER® tweet, multimedia messaging services (MMS), and/or other type of communi-cation technology. In various embodiments, a channel may be hosted or provided by a data partner. In various embodi-ments, the distribution channel may comprise at least one of a merchant website, a social media website, affiliate or partner websites, an external vendor, a mobile device com-munication, social media network, and/or location based service. Distribution channels may include at least one of a merchant website, a social media site, affiliate or partner websites, an external vendor, and a mobile device commu-nication. Examples of social media sites include FACE-BOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

The detailed description of various embodiments herein makes reference to the accompanying drawings and pic-tures, which show various embodiments by way of illustra-tion. While these various embodiments are described in sufficient detail to enable those skilled in the art to practice the disclosure, it should be understood that other embodi-ments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. More-over, any of the functions or steps may be outsourced to or performed by one or more third parties. Modifications, additions, or omissions may be made to the systems, appa-ratuses, and methods described herein without departing from the scope of the disclosure. For example, the compo-nents of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this docu-ment, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A method of causing or enhancing the perception of color, the method comprising:

varying a parameter of electromagnetic stimulation of an electromagnetic stimulation device based on which color is detected by a visualization device that is used in conjunction with the electromagnetic stimulation device; and stimulating a hearing pathway, a smell pathway, or a taste pathway of a blind or visually impaired person with the electromagnetic stimulation device according to the parameter of electromagnetic stimulation.

2. The method of claim 1, wherein varying the parameter of electromagnetic stimulation further comprises controlling the variation of the parameter of electromagnetic stimulation via a wireless signal to the electromagnetic stimulation device.

3. The method of claim 2, wherein the wireless signal is provided in response to what is detected by the visualization device wherein the wireless signal is one of: a radio frequency signal and an optical signal.

4. The method of claim 1, wherein the parameter of electromagnetic stimulation is a frequency of stimulation, and wherein varying the parameter of electromagnetic stimulation of the electromagnetic stimulation device comprises frequency modulation of stimulation of the electromagnetic stimulation device.

5. The method of claim 4, further comprising personalized tuning of the parameter of electromagnetic stimulation, such that the frequency of stimulation provides optimal perception of a color detected by the visualization device for each individual blind or visually impaired person.

6. The method of claim 5, comprising:

showing the blind or visually impaired person a known color;

optimizing a preferred frequency of stimulation by repeating the process of:

setting the frequency of stimulation to a first frequency;

setting the frequency of stimulation to a second frequency;

obtaining feedback from the blind or visually impaired person as to which of the first frequency and the second frequency caused better perception of the known color, and using the feedback to set a preferred frequency; and setting the frequency of stimulation at the preferred frequency.

7. The method of claim 5, comprising:

tuning a first preferred frequency for a first color, based on a first known color, to an optimal frequency for an individual to perceive the first known color;

saving the first preferred frequency for the first color;

tuning a second preferred frequency for a second color, based on a second known color, to an optimal frequency for the individual to perceive the second known color;

saving the second preferred frequency for the second color; and varying the frequency of stimulation of the electromagnetic stimulation device based on the saved first preferred frequency when the first color is viewed by the visualization device, and based on the saved second preferred frequency when the second color is viewed by the visualization device.

8. The method of claim 4, wherein the frequency of stimulation is in the range of 15 Hz to 25 Hz for the color yellow, and wherein the frequency of stimulation is in the range of 60 to 120 Hz for the color blue.

9. The method of claim 1, wherein the stimulating is through electrodes connected with an ear or an acoustic nerve.

10. The method of claim 1, wherein the stimulating is through electrodes connected with a nose.

11. The method of claim 1, wherein the stimulating is through electrodes connected with a mouth or a tongue.

\* \* \* \* \*